US006469206B2

(12) United States Patent
Hembre et al.

(10) Patent No.: US 6,469,206 B2
(45) Date of Patent: Oct. 22, 2002

(54) PROCESS FOR THE PREPARATION OF TRIFLIC ANHYDRIDE

(75) Inventors: Robert Thomas Hembre, Johnson City, TN (US); Robert Lin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/792,995

(22) Filed: Feb. 26, 2001

(65) Prior Publication Data

US 2002/0002301 A1 Jan. 3, 2002

Related U.S. Application Data

(60) Provisional application No. 60/187,832, filed on Mar. 8, 2000.

(51) Int. Cl.$^7$ .............................................. C07C 303/00
(52) U.S. Cl. ...................... 562/872; 562/873; 562/886; 562/887; 562/892; 562/893; 562/894; 562/897; 562/898
(58) Field of Search ................................ 562/872, 873, 562/886, 887, 892, 893, 894, 897, 898

(56) References Cited

U.S. PATENT DOCUMENTS

| 2,732,398 A | 1/1956 | Brice et al. |
| 5,169,994 A | 12/1992 | Sumner, Jr. et al. |

FOREIGN PATENT DOCUMENTS

| JP | 11-236365 | 8/1999 |
| JP | 11-236366 | 8/1999 |

OTHER PUBLICATIONS

Karger et al, Journal of Organic Chemistry, vol. 36, No. 4, 1971, pp. 528–531.*
Karger et al, Journal of Organic Chemistry, vol. 36, No. 4, 1971, pp. 528–531.*
Effenberger et al, Angew. Chem. Internat. Edit. vol. 11, No. 4, 1972, pp. 299–300 and Effenberger et al, Chem. Ber. vol. 116, p. 1183, 1983.*
Olah et al, Journal of Organic Chemistry, vol. 27, 1962, pp. 2667–2668.*
Aldrich Handbook of Fine Chemicals, 1996–97.*
F. Effenberger, et al., Chem. Ber., vol. 116, No. 3, Mar. 3, 1983, pp. 1183–1194.
Patent Abstract of Japan, vol. 1998, No. 10, JP 10114734 published May 6, 1998.
Haszeldine et al, J. Chem. Soc., 1954, pp. 4228–4232.
Waller et al, Chem. Ind., 1998, 75, pp. 289–305.
Ritter, Synthesis, 1993, pp. 735–762.
Stang et al. Synthesis, 1982, pp. 85–126.
Howells et al, Chem. Rev., 1977, vol. 77, pp. 69–92.
Burdon et al, J. Chem. Soc., 1957, pp. 2574–2578.
Gramstad et al, J. Chem. Soc., 1957, pp. 4069–4079.
Effenberger et al., Ang. Chem. Intl. Ed. Engl., 1972, vol. 11, No. 4, pp. 299–300.
Blake et al, J. Chem. Soc., Perkin II, (B), 1976, pp. 1533–1536.

* cited by examiner

*Primary Examiner*—Paul J. Killos
*Assistant Examiner*—Héctor M Reyes
(74) *Attorney, Agent, or Firm*—Michael J. Blake; Bernard J. Graves, Jr.

(57) ABSTRACT

Disclosed is a process for the preparation of trifluoromethanesulfonic acid anhydride by the steps of (1) forming a mixed anhydride comprising a trifluoromethanesulfonyl acyl residue and a carboxyl residue by contacting trifluoromethanesulfonic acid or a derivative thereof with a carboxyl compound selected from ketene, dialkyl ketenes, carboxylic acids, and derivatives of carboxylic acids and (2) subjecting the mixed anhydride to reactive distillation wherein the mixed anhydride undergoes disproportionation to produce triflic anhydride and a higher boiling carboxylic acid anhydride.

14 Claims, No Drawings

PROCESS FOR THE PREPARATION OF TRIFLIC ANHYDRIDE

CROSS REFERENCE TO RELATED APPLICATION

This application claims the benefit of provisional application Serial No. 60/187,832 filed Mar. 8, 2000.

FIELD OF THE INVENTION

This invention pertains to a process for the preparation of trifluoromethanesulfonic acid anhydride (triflic anhydride) by the disproportionation of a mixed anhydride comprising a trifluoromethane-sulfonyl acyl residue and a carboxyl residue. More particularly, this invention pertains to a process for the preparation of trifluoromethane-sulfonic acid anhydride by the steps of (1) forming a mixed anhydride comprising a trifluoromethanesulfonyl acyl residue and a carboxyl residue by contacting trifluoromethanesulfonic acid or a derivative thereof with a carboxyl compound selected from ketene, dialkyl ketenes, carboxylic acids, and derivatives of carboxylic acids and (2) subjecting the mixed anhydride to reactive distillation wherein the mixed anhydride undergoes disproportionation to produce triflic anhydride and a higher boiling carboxylic acid anhydride.

BACKGROUND OF THE INVENTION

The preparation of trifluoromethanesulfonic (triflic) acid was first reported in 1954 by R. N. Hazeldine and J. M. Kidd, *J. Chem. Soc.* 1954, 4228. It is widely used in organic synthesis both for research and commercial interests. See, for example, F. J. Waller, D. Ramprasad, A. G. M. Barrett, D. C. Braddock, *Chem. Ind.,* 1998, 75, 289–305; Kurt Ritter, *Synthesis,* 1993, 735–62; P. J. Stang, M. Hanack and L. R. Subramanian, *Synthesis,* 1982, 85; and R. D. Howells and J. D. McCown *Chem. Rev.,* 1977, 77, 69–92. Synthesis of triflic anhydride was first reported by Brice and Trott in U.S. Pat. No. 2,732,398 (1956) and in the following year higher yield preparations via treatment of trifluoromethanesulfonic acid with phosphorus pentoxide were reported by Burdon et al, *J. Chem. Soc.,* 1957, 2574 and Gramstad et al., *J. Chem. Soc.,* 1957, 4069.

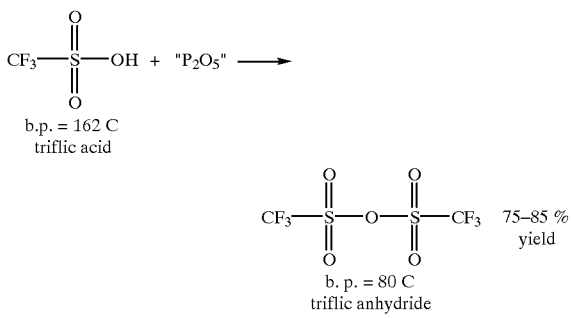

In the ensuing four decades this phosphorus pentoxide approach has remained the preferred synthetic method. Japanese Published Patent Documents JP 11-236,365 and JP 11-236,366 describe the preparation of triflic anhydride by the reaction of triflic acid with phosphorus pentachloride or phosphorus trichloride and chlorine. Such reagents are inefficient as they generate a volume of non-recyclable byproducts as large as, or larger than, that of the desired product. These reagents, therefore, are not well suited for large-volume manufacture of triflic anhydride.

BRIEF SUMMARY OF THE INVENTION

We have discovered an improved process for the preparation of triflic acid anhydride which does not require the use of a phosphorus reagent. The present invention provides a process for the coproduction of trifluoro-methanesulfonic acid anhydride and a carboxylic acid anhydride which comprises the steps of:
(1) forming a mixed anhydride comprising a trifluoromethanesulfonyl acyl residue and a carboxyl residue by contacting trifluoromethanesulfonic acid or an acid halide thereof, e.g., trifluoromethanesulfonyl chloride, with a carboxyl compound selected from ketene, dialkyl ketenes, carboxylic acids, salts of carboxylic acids, and carboxylic acid halides; and
(2) subjecting the mixed anhydride to reactive distillation to produce triflic anhydride and a higher boiling carboxylic acid anhydride.

In an especially preferred embodiment of the present invention, triflic acid is reacted with dimethylketene to produce the mixed anhydride isobutyryl triflate (or trifluoromethanesulfonyl isobutyrate), i.e., a mixed anhydride having the formula:

$$F_3CSO_2-O-C(O)-CH(CH_3)_2$$

which then is disproportionated by means of reactive distillation to produce the lower boiling triflic acid anhydride and the higher boiling isobutyric anhydride. Our novel process provides a number of advantages such as producing triflic anhydride in high yields, being readily adaptable to continuous operation and producing essentially no waste products.

DETAILED DESCRIPTION

The mixed anhydrides which may be utilized in the present process have the general formula $$F_3CSO_2-O-C(O)-R \qquad (I)$$

wherein R represents the residue of an aliphatic carboxylic acid, e.g., an alkanoic acid, containing from 2 to 8 carbon atoms, e.g., acetic, propionic, n- and i-butyric, hexanoic, 2-ethylhexanoic, and the like. The mixed anhydrides may be prepared by a number of methods well known in the literature. For instance, Epple, *Ang. Chem. Intl. Ed. Engl.,* 1972, 11, 299, discloses the preparation of mixed anhydrides useful in the present invention by the reaction of trifluoromethanesulfonyl chloride with either a carboxylic acid or salts of a carboxylic acid and the reaction of triflic acid with a carboxylic acid chloride. Examples of the carboxylic acid salts and acid halides which may be used in these known processes include alkanoyl chlorides and bromides which contain from 2 to 8 carbon atoms and alkali metal, e.g., potassium, lithium and sodium alkanoates which contain from 2 to 8 carbon atoms. Although these methods may not be preferred for commercial-scale operation, they may be used to generate the mixed anhydrides useful in the process of our invention. The preferred methods for preparing a mixed anhydride comprises the reaction of triflic acid with a ketene and the carbonylation of alkyl triflates catalyzed by transition metals according to known procedures. The reaction of triflic acid with a ketene is particularly preferred since the reaction occurs rapidly without the need for a catalyst or catalyst promoters and the mixed anhydride is produced in a state of purity which can be submitted directly to a reactive distillation column without purification.

Triflic acid and a ketene may be reacted according to known procedures, e.g., see Blake, et al., *J. Chem. Soc.,(B)*

1976, 1533–36, to produce a mixed anhydride. The preferred ketenes for the process described herein are ketene and, especially, dimethylketene. The addition of a ketene to triflic acid can be carried out at a temperature in the range of about −76 to 70° C., preferably about −20 to 40° C. The mole ratio of triflic acid:ketene may be in the range of about 100:1 to 0.75:1, preferably about 10:1 to 0.9:1. A chlorinated solvent such as dichloroethane may be used but normally is not preferred. Pressure is not an important feature of the triflic acid-ketene reaction which normally is carried out at ambient pressure although low pressure or moderately above ambient pressure may be used.

In the second step of the process, the mixed anhydride of formula (I) Is subjected to reactive distillation wherein the mixed anhydride is disproportionated to produce triflic acid anhydride as a lower boiling product and a carboxylic acid anhydride, i.e., an anhydride having the formula:

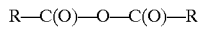

wherein R is defined above, as a higher boiling product. In order for the disproportionation to operate in an ideal fashion the mixed anhydride should have a boiling point intermediate between the two product anhydrides. Normally, this is the case for mixed anhydrides. However, because triflic acid (normal b.p.=166° C.) and the carboxylic acid residues which are components of the mixed anhydride are intermediates in the mixed anhydride disproportionation, both triflic acid and the carboxylic acid preferably have boiling points that are between those of triflic anhydride and the anhydride derived from the carboxylic acid. Acetic anhydride (normal b.p.=140° C.) and propionic anhydride (normal b.p.=167° C.) have boiling points that are either lower than or similar to that of triflic acid. Because isobutyric anhydride has an appropriate boiling point (normal b.p.=182° C.) and a ketene precursor (i.e., dimethylketene) that can be generated in a continuous fashion (see Sumner et al. U.S. Pat. No. 5,169,994), trifluoro-methanesulfonyl isobutyrate (or isobutyryl triflate) derived from triflic acid and dimethylketene is the most preferred mixed anhydride for the continuous production of triflic anhydride.

The reactive distillation column is operated at temperatures between the boiling points of triflic anhydride and the carboxylic anhydride being produced at the pressure at which the column is operated. For the production of triflic anhydride at ambient pressure the temperature at the top or head of the column is in the range of about 70 to 90° C. Column head temperatures in the range of about 75 to 85° C. are preferred. At subambient pressure the temperature at the head of the column may be in the range of about 35 to 75° C. with a range of 50 to 70° C. being preferred. The base of the column at ambient pressure typically is maintained at a temperature in the range of about 110 to 220° C., preferably about 120 to 200° C., the specific temperature depending upon the particular carboxylic acid anhydride being produced. When ketene is used to generate the mixed anhydride such that disproportionation yields acetic anhydride at the base of the column, the temperature at the bottom or base of the reactive distillation column is in the range of about 110 to 150° C. A base temperature in the range of 125 to 145° C. is preferred. When dimethylketene is used to generate the mixed anhydride such that disproportionation produces isobutyric anhydride, the temperature at the bottom or base of the reactive distillation column, if the column is operated at ambient pressure or slightly above or below, is in the range of about 150 to 200° C., preferably in the range of 170 to 190° C. Operation of the reactive distillation column at reduced pressure may be preferred to avoid undesired side reactions of triflic anhydride. It is desirable to maintain a highest temperature less than 160° C. in the base of the column and thus an appropriately reduced pressure may be preferred dependent on the carboxylic anhydride being produced by the reactive distillation. The reactive distillation uses a column with plates and/or trays and/or packing that cause numerous equilibrations to achieve total disproportionation.

Although not essential, it is preferred to carry out the disproportionation of the mixed anhydride in the presence of an acidic catalyst, e.g., a strong acid such as sulfuric acid and polymeric resins containing acidic functional groups, e.g., polymer-bound sulfonic acids such as those derived from vinylbenzenesulfonic acid and divinylbenzene. The acidic polymeric resins, e.g., ion exchange resins such as those sold under the tradenames Nafion and Duolite, may be introduced into the distillation apparatus and/or incorporated into the distillation apparatus.

The process of the present invention may be operated in a batch, continuous or semi-continuous manner. For example, the process may be carried out by first reacting a ketene and triflic acid in a reaction vessel equipped with a distillation column. This vessel containing the mixed anhydride then may be heated to effect reactive distillation of the contents of the reaction vessel and recover triflic anhydride from the upper section of the distillation column. The process for the coproduction of triflic anhydride and a carboxylic acid anhydride, e.g., acetic or isobutyric anhydride, preferably is carried out in a continuous or semi-continuous manner comprising the steps of: (1) introducing a ketene reactant such as ketene or dimethylketene and triflic acid to a reaction vessel wherein the ketene reactant and triflic acid react to form a product comprising a mixed anhydride, e.g., acetyl triflate or isobutyryl triflate; (2) removing product from the reaction vessel and introducing it into the mid-section of a reactive distillation column wherein the mixed anhydride disproportionates to form triflic anhydride and a carboxylic anhydride, e.g. acetic or isobutyric anhydride; (3) removing triflic anhydride from the upper section of the reactive distillation column; and (4) removing a carboxylic anhydride from the lower section of the reactive distillation column.

The mixed anhydride produced by the reaction of a ketene and triflic acid alternatively may be distilled at low temperature to avoid its disproportionation and provide a purified mixed anhydride. To produce a purified mixed anhydride the distillation temperature must be less than about 50° C., e.g., 20 to 45° C. The stability of triflate mixed anhydrides to low temperature distillation is reported by Epple, et al. (loc.cit.). Because the reaction of a slight excess of ketene with triflic acid can be carried out at low temperatures, a unique high-yield process for the production of acetyl triflate or isobutyryl triflate is obtained if the so-produced mixed anhydride is distilled at low pressure.

An alternative means for operating the process of the present invention involves the general procedures described herein for the preparation of a mixed anhydride in combination with reactive distillation to coproduce triflic anhydride and a carboxylic anhydride. This more general embodiment of the invention comprises the steps of (1) preparing in a reaction vessel a mixed anhydride having the formula

wherein R represents the residue of an aliphatic carboxylic acid containing from 2 to 8 carbon atoms; (2) removing product from the reaction vessel and introducing it into the mid-section of a reactive distillation column wherein the mixed anhydride disproportionates to form triflic anhydride and a carboxylic anhydride; (3) removing triflic anhydride from the upper section of the reactive distillation column; and (4) removing a carboxylic anhydride from the lower section of the reactive distillation column.

Another mode of continuous or semi-continuous operation of the process, which may be but is not necessarily used in conjunction with the first aspect of the invention, comprises the steps of (1) introducing a ketene, preferably dimethyl ketene, and triflic acid directly into a reactive distillation column wherein the ketene and triflic acid react to form a mixed anhydride which disproportionates to form triflic anhydride and a carboxylic anhydride; (2) removing triflic anhydride from the upper section of the reactive distillation column; and (3) removing higher boiling liquid comprising a carboxylic anhydride from the lower section of the reactive distillation column.

The invention has been described in detail with particular reference to preferred embodiments thereof, but it will be understood that variations and modifications can be effected within the spirit and scope of the invention.

We claim:

1. Process for the coproduction of trifluoromethanesulfonic acid anhydride and a carboxylic acid anhydride which comprises the steps of:
   (1) forming a mixed anhydride comprising a trifluoromethanesulfonyl acyl residue and a carboxyl residue by contacting trifluoromethanesulfonic acid (triflic acid) or an acid halide thereof with a carboxyl compound selected from ketene, dialkyl ketenes, carboxylic acids, salts of carboxylic acids, and carboxylic acid halides; and
   (2) subjecting the mixed anhydride to reactive distillation to produce triflic anhydride and a higher boiling carboxylic acid anhydride.

2. Process according to claim 1 which comprises the steps of:
   (1) forming a mixed anhydride comprising a trifluoromethanesulfonyl acyl residue and a carboxyl residue by contacting triflic acid with a carboxyl compound selected from ketene and dimethylketene; and
   (2) subjecting the mixed anhydride to reactive distillation to produce triflic anhydride and a higher boiling carboxylic acid anhydride.

3. Process according to claim 2 wherein step (1) comprises contacting triflic acid with a carboxyl compound selected from ketene and dimethyl-ketene at a temperature of about −20 to 40° C. using a triflic acid:carboxylic compound mole ratio of about 10:1 to 0.9:1.

4. Process according to claim 1 which comprises the steps of:
   (1) forming a mixed anhydride by contacting triflic acid with ketene at a temperature of about −20 to 40° C. using a triflic acid:ketene mole ratio of about 10:1 to 0.9:1; and
   (2) subjecting the mixed anhydride to reactive distillation in a distillation column operated at a head temperature of about 70 to 90° C. and a column base temperature of about 110 to 150° C. to produce triflic anhydride and acetic anhydride.

5. Process according to claim 1 which comprises the steps of:
   (1) forming a mixed anhydride by contacting triflic acid with dimethyl-ketene at a temperature of about −20 to 40° C. using a triflic acid:dimethylketene mole ratio of about 10:1 to 0.9:1; and
   (2) subjecting the mixed anhydride to reactive distillation in a distillation column operated at a column head temperature of about 50 to 90° C. and a column base temperature of about 150 to 200° C. to produce triflic anhydride and isobutyric anhydride.

6. Process for the coproduction of trifluoromethanesulfonic acid anhydride (triflic anhydride) and a carboxylic acid anhydride which comprises the steps of: (1) introducing a ketene reactant and triflic acid to a reaction vessel wherein the ketene reactant and triflic acid react to form a product comprising a mixed anhydride; (2) removing product from the reaction vessel and introducing it into the mid-section of a reactive distillation column wherein the mixed anhydride disproportionates to form triflic anhydride and a carboxylic acid anhydride; (3) removing triflic anhydride from the upper section of the reactive distillation column; and (4) removing a carboxylic anhydride from the lower section of the reactive distillation column.

7. Process according to claim 6 wherein step (1) comprises introducing ketene and triflic acid to a reaction vessel wherein the ketene and triflic acid react at a temperature of about −20 to 40° C. using a triflic acid:ketene mole ratio of about 10:1 to 0.9:11 to form a product comprising a mixed anhydride; and step (2) comprises removing product from the reaction vessel and introducing it into the mid-section of a reactive distillation column operated at a column head temperature of about 70 to 90° C. and a column base temperature of about 110 to 150° C. to produce triflic anhydride and acetic anhydride.

8. Process according to claim 6 wherein step (1) comprises introducing dimethylketene and triflic acid to a reaction vessel wherein the dimethyl ketene and triflic acid react at a temperature of about −20 to 40° C. using a triflic acid:dimethyl ketene mole ratio of about 10:1 to 0.9:11 to form a product comprising a mixed anhydride; and step (2) comprises removing product from the reaction vessel and introducing it into the mid-section of a reactive distillation column operated at a column head temperature of about 50 to 90° C. and a column base temperature of about 150 to 200° C. to produce triflic anhydride and isobutyric anhydride.

9. Process for the coproduction of trifluoromethanesulfonic acid anhydride (triflic anhydride) and a carboxylic acid anhydride which comprises the steps of (1) preparing in a reaction vessel a mixed anhydride having the formula

$$F_3CSO_2—O—C(O)—R \qquad (I)$$

wherein R represents the residue of an aliphatic carboxylic acid containing from 2 to 8 carbon atoms; (2) removing product from the reaction vessel and introducing it into the mid-section of a reactive distillation column wherein the mixed anhydride disproportionates to form triflic anhydride and a carboxylic anhydride; (3) removing triflic anhydride from the upper section of the reactive distillation column; and (4) removing a carboxylic anhydride from the lower section of the reactive distillation column.

10. A process according to claim 9 wherein the reactive distillation column is operated at a column head temperature in the range of about 50 to 90° C. and a column base temperature of about 150 to 220° C.

11. Process according to claim 10 wherein step (1) comprises the reaction of trifluoromethanesulfonyl chloride with a carboxylic acid or a salt of a carboxylic acid containing 2 to 8 carbon atoms.

12. Process according to claim 10 wherein step (1) comprises the reaction of a carboxylic acid chloride containing 2 to 8 carbon atoms with triflic acid or a salt of triflic acid.

13. Process for the coproduction of trifluoromethanesulfonic acid anhydride (triflic anhydride) and a carboxylic anhydride which comprises the steps of: (1) introducing a ketene reactant and trifluoromethanesulfonic acid (triflic acid) acid directly into a reactive distillation column wherein the ketene reactant and triflic acid react to form a mixed anhydride which disproportionates to form triflic anhydride and a carboxylic anhydride; (2) removing triflic anhydride from the upper section of the reactive distillation column; and (3) removing a carboxylic anhydride from the lower section of the reactive distillation column.

14. Process according to claim 13 wherein the ketene reactant is selected from ketene and dimethylketene.

* * * * *